United States Patent [19]
Bussian et al.

[11] Patent Number: 4,802,361
[45] Date of Patent: Feb. 7, 1989

[54] PRODUCTION STREAM ANALYZER

[75] Inventors: Alfred E. Bussian, Spring; Thomas M. Williams, Houston; Paul D. Carmichael, Houston; Hans J. Paap, Houston, all of Tex.

[73] Assignee: Texaco Inc., White Plains, N.Y.

[21] Appl. No.: 346,682

[22] Filed: Feb. 8, 1982

[51] Int. Cl.[4] ............................................. G01N 33/22
[52] U.S. Cl. .................................... 73/61.1 R; 73/53
[58] Field of Search ............... 73/53, 61 R, 61.1 R; 324/61 R; 378/51, 54, 55

[56] References Cited

U.S. PATENT DOCUMENTS

| | | | |
|---|---|---|---|
| 2,720,624 | 10/1955 | Gunst et al. | 324/61 QL |
| 2,953,681 | 9/1960 | Frazier | 378/51 |
| 3,778,706 | 12/1973 | Thompson | 324/61 R |
| 3,977,234 | 8/1976 | Lynch et al. | 73/53 |
| 4,112,744 | 9/1978 | Tassano | 73/61.1 R |
| 4,266,188 | 5/1981 | Thompson | 324/65 R |
| 4,266,425 | 5/1981 | Allport | 73/61 R |
| 4,289,020 | 9/1981 | Paap | 73/61.1 R |
| 4,352,288 | 10/1982 | Paap et al. | 73/61 R |
| 4,359,638 | 11/1982 | Allport | 324/61 R |
| 4,364,262 | 12/1982 | Woodle et al. | 73/53 |
| 4,458,524 | 7/1984 | Meador et al. | 73/61.1 R |
| 4,644,263 | 2/1987 | Johnson | 324/65 P |

Primary Examiner—William A. Cuchlinski, Jr.
Assistant Examiner—W. Morris Worth
Attorney, Agent, or Firm—Robert A. Kulason; Ronald G. Gillespie

[57] ABSTRACT

A production stream analyzer, which analyzes a flowing crude oil production stream in a conduit, includes a temperature sensor, a capacitance measuring device and a densitometer which provide corresponding temperature, capacitance and density signals, respectively. An output circuit provides an output signal corresponding to the quantity of at least one constituent of the production stream in accordance with the temperature, the capacitance and the density signals.

10 Claims, 1 Drawing Sheet

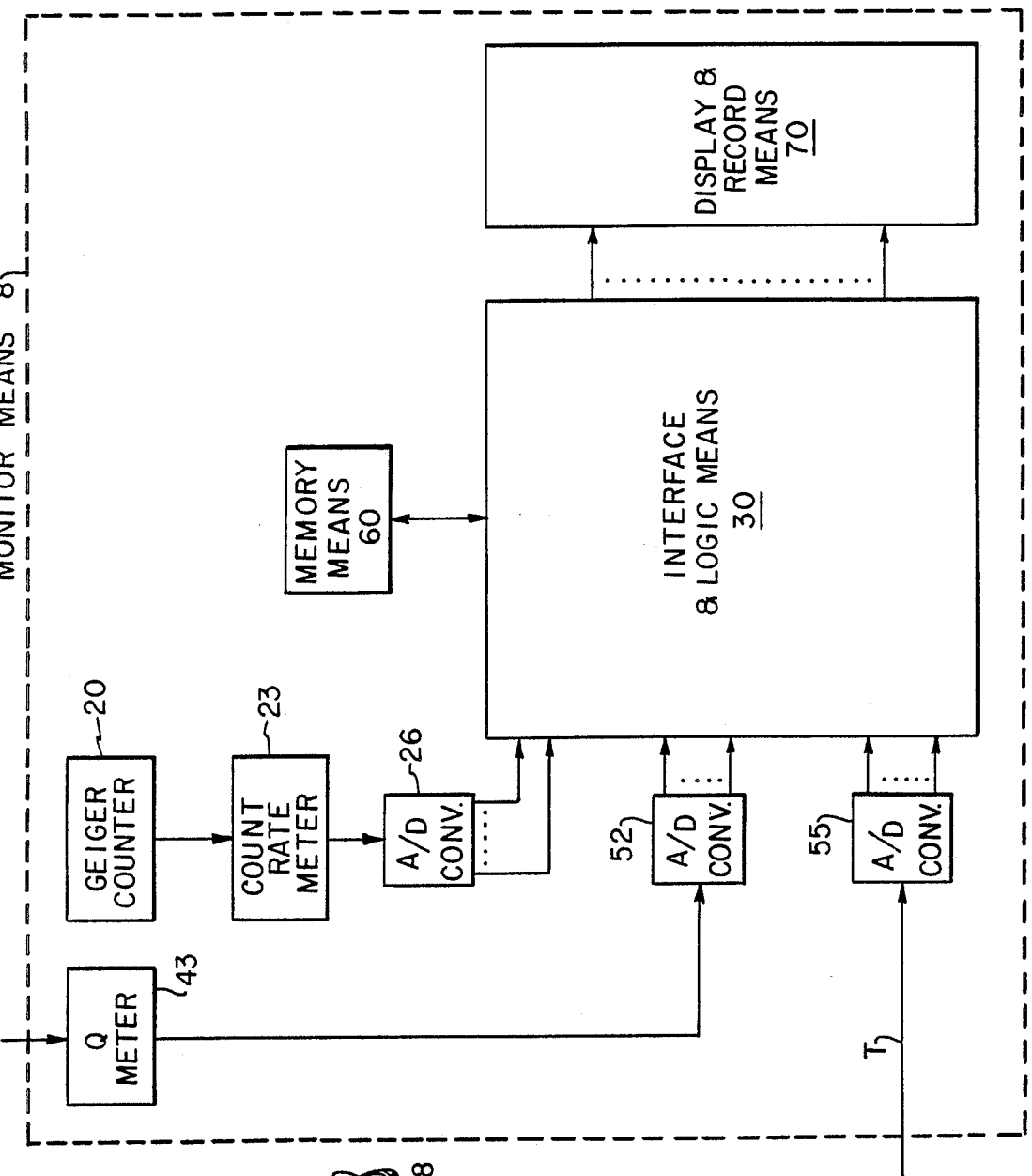

PRODUCTION STREAM ANALYZER

BACKGROUND OF THE INVENTION

Field of the Invention

The present invention relates to monitors in general and, more particularly, to monitors used in the petroleum industry.

SUMMARY OF THE INVENTION

A production stream analyzer analyzes a flowing crude oil production stream and provides a signal corresponding to at least one constituent's quantity of the production stream. The analyzer includes a temperature sensor, a device and a densitometer determining the temperature, the capacitance and the density of the production stream, respectively, and providing corresponding temperature, capacitance and density signals, respectively. An output circuit provides the signal corresponding to the quantity of the constituent of the production stream in accordance with the temperature, capacitance and density signals.

The objects and advantages of the invention will appear more fully hereinafter from a consideration of the detailed description which follows, taken together with the accompanying drawings wherein one embodiment of the invention is illustrated by way of example. It is to be expressly understood, however, that the drawings are for illustration purposes only and are not to be construed as defining the limits of the inventions.

DESCRIPTION OF THE DRAWINGS

FIG. 1 is a simplified partial block diagram and partial schematic of a production stream analyzer constructed in accordance with the present invention.

FIG. 2 is a detailed block diagram of the monitor means shown in FIG. 1.

DESCRIPTION OF THE INVENTION

Theory

Production streams in the recovery of crude oil from an earth formation generally are not 100% crude oil but contain in various degrees water (or brine) or gas. The present invention has discovered a relationship among characteristics of a crude oil production stream that allows the determination of the quantities of those production stream constituents.

Consider a mixture of oil, water and gas in the crude oil production stream where the continuous phase is non-conducting, i.e. gas dispersed in a water-in-oil emulsion or any mixture of oil and water dispersed in gas.

Let
$v_o$ = fractional volume of oil in the production stream
$v_w$ = fractional volume of water in the production stream
$v_g$ = fractional volume of gas in the production stream It follows that $$v_o + v_w + v_g = 1 \tag{1}$$

Measured values of density $\rho_m$ and dielectric constant $k_m$ are expressed in terms of $v_o$ and $v_w$ as follows:

$$\rho_m = (\rho_w - \rho_g)v_w + (\rho_o - \rho_g)v_o + \rho_g \tag{2}$$

$$k_m = k_m(v_w, v_o) \tag{3}$$

where $\rho_o$ = density of oil, $\rho_w$ = density of water and $\rho_g$ = density of gas.

Assuming that an explicit function $k_m(v_w, v_o)$ can be found, then equations (2) and (3) can be solved for $v_w$ and $v_o$. Water cut (1) can then be determined using $$L = v_w/(v_w + v_o) \tag{4}$$

The density, which is related to the constituent volumes of the production stream as hereinafter described, is determined with a gamma ray densitometer which irradiates the production stream with gamma radiation. The gamma radiation, after passing through the production stream, is detected and a count rate C is developed. The count rate C is related to the measured density $\rho_m$ in the following equation $$\rho_m = K \ln (C/C_0) \tag{5}$$

where K and $C_0$ are calibration constants which are predetermined. Density $\rho_m$ is related to the densities of the different constituents of the production stream as shown in equation (2).

Using equations (2) and (4) the fractional oil and water volumes can be written as $$v_o = [(1-L)(\rho_m - \rho_g)]/[L(\rho_w - \rho_g) + (\rho_o - \rho_g)(1-L)] \tag{6}$$

and $$v_w = [L(\rho_m - \rho_g)]/[(1-L)(\rho_o - \rho_g) + L(\rho_w - \rho_g)] \tag{7}$$

The fractional volume of liquid is given by $$v_l = v_w + v_o \tag{8}$$

The dielectric constant can be determined by measuring the capacitance of the production stream and using the following equation $$k_m = (a + bC_m)/(c + C_m) \tag{9}$$

where $C_m$ is the measured capacitance and a, b, c are calibration constants which are predetermined. a, b, and c were determined with the probe filled with air, oil and water. Equation (9) was derived on the assumption that the measured capacitance is a combination of the capacitance of the fluid and two intrinsic capacitances of a capacitance probe, one in series and one in parallel with the fluid capacitance.

It remains to determine an explicit expression for equation (3). A general relationship for a mixture of two materials where particles of material p are dispersed in material m is given by equation (10). That equation appears in several publications such as T. Hanai, Kolloid-Festschrift 175, 61 (1960), Kyoto University Institute for Chem. Research Bulletin, 39, 431 (1961) and P. N. Sen. C. Scala, and M. H. Cohen, Geophysics 46, 781 (1981).

$$[(\epsilon - \epsilon_p)/(\epsilon_m - \epsilon_p)](\epsilon_m/\epsilon)^D = 1 - \phi_p \tag{10}$$

where
$\epsilon$ = complex relative permittivity of mixture
$\epsilon_m$ = complex relative permittivity of continuous phase
$\epsilon_p$ = complex relative permittivity of disperse phase
$\phi_p$ = volume fraction of dispersed phase
D = depolarizaion factor ($0 \leq D \leq 1$)

The complex relative permittivity is given by $$\epsilon = k + i(\sigma/\omega\epsilon_o)$$

where
k=dielectric constant
$\sigma$=conductivity
$\epsilon_o$=permittivity of vacuum
$\omega = 2\pi X$ frequency For spherical dispersed particles, the exponent in equation (10) is ⅓.

A two step application of equation (10) was made to the experimental data. Equation (10) is first applied by assuming a water-in-oil emulsion or mixture where the oil is taken to be an insulator and that the water is a conductor. In the second step, gas is assumed to be immersed in the emulsion where both the gas and the emulsion are assumed to be insulators. The first application of equation (10) gives $$L = 1 - (k_o/k_l)^n \quad (11)$$

The second application of equation (10) gives $$v_l = (k_l/k_m)^m [(k_m - k_g)/(k_l - k_g)] \quad (12)$$

where
n=depolarization factor for water immersed in oil
m=depolarization factor for gas immersed in emulsion
$k_g$=gas dielectric constant
$k_l$=dielectric constant of water-in-oil emulsion or mixture
$k_o$=dielectric constant of oil In principle, one can now derive an explicit function $$k_m = k_m(v_w, v_o)$$

from equations (11) and (12). Then using equations (2), (3) and (4), one can determine water cut. As a practical matter, L will have to be determined numerically using a computer or microprocessor.

Equations (11) and (12) have been derived using equation (10) for bubble flow. However, equation (10) is a general relationship which can, in principle, be applied to any flow regime.

WATER-IN-CRUDE MONITOR

The foregoing theory shows the interrelationship of the different constituents of the crude oil production stream. Those equations are all well known in the art and are part of the public domain. The present invention utilizes a novel relationship between those equations to determine water cut. The following describes a system similar to one which demonstrates the feasibility of the technique in the laboratory. With reference to FIG. 1, the production stream, consisting of various phases of oil, water and gas flows through a pipe 1. A ten microcurie Cs[137] gamma ray source 4 is mounted within a lead collimator 6 and irradiates the production stream in pipe 1 with gamma radiation. Monitor means 8 receives the gamma radiation after passage through the production stream.

A capacitance probe 12 is inserted in pipe 1 and electrically connected to monitor means 8. A temperature sensor 18 senses the temperature of the production stream and provides a corresponding signal T to monitor means 8.

Monitor means 8 provides an indication of the water content of the production stream in accordance with the received signal T, the received gamma radiation and the capacitance of the production stream as hereinafter explained.

Referring now to FIG. 2, a geiger counter 20 in monitor means 8 provides pulses in accordance with the gamma radiation that has passed through the production stream. A count rate meter 23 receives the pulses from geiger counter 20 and provides a signal corresponding to the count rate of the pulses from geiger counter 23 and hence to the detected gamma radiation. The count rate signal from the meter 23 is converted to digital signals by an analog-to-digital converter 26 which provides the digital signals to interface and logic means 30.

Capacitance probe 12 is electrically connected to a Q meter 43, such as manufactured by Hewlett-Packard as Model 4342A, which provides a signal to an analog-to-digital converter 52. Converter 52 provides corresponding digital signals to address signal means.

Signal T from temperature sensor 18 is converted to digital signals by an analog-to-digital converter 55 which provides the digital signals to address signal means.

Interface and logic means 30 provides memory address signals to memory means 60 to select information stored in memory means 60. Different volumes, in digital form, of constituents of the production stream are stored in memory means 60. In the present example, for each combination of temperature, measured capacitance and detected gamma radiation there is stored a corresponding value for L, as determined by prior calibration. The address signals cause memory means 60 to select the appropriate water fractional volume of the production stream and provide signals back to interface and logic means 30 which in turn provides signals to display means 70 to display. Of course, it would be obvious to one skilled in the art that the gas, crude oil, and water fractional volumes may also be stored. If the water is brine then the salt content may be stored in lieu of the fractional water volume value if so desired.

The crude oil production stream analyzer as hereinbefore described determines the water cut of a production stream in accordance with the density, the capacitance and the temperature of the production stream.

What is claimed is:

1. A production stream analyzer for use with a flowing crude oil production stream which also includes water and gas in a conduit comprises:
   a sensor sensing the temperature of the flowing production stream and providing a temperature signal representative thereof,
   monitoring means for monitoring the capacitance of the production stream and providing a corresponding capacitance signal,
   a densitometer measuring the density of the production stream and providing a density signal corresponding thereto, and
   output means connected to the sensor, to the monitoring means and to the densitometer for providing output signals corresponding to the quantity of at least one constituent of the production stream in accordance with the temperature, the capacitance and the density signals.

2. An analyzer as described in claim 1 in which the capacitance monitoring means includes
   a capacitance probe located in the production stream, and means connected to the capacitance probe for providing the capacitance signal in accordance with the capacitance sensed by the capacitance probe.

3. An analyzer as described in claim 2 in which the density measuring means includes means for irradiating the production stream with gamma radiation in a manner so that the gamma radiation passes through the production stream, and means responsive to the gamma radiation that has passed through the production stream for providing a signal corresponding to the density of the production stream.

4. An analyzer as described in claim 3 in which the output means includes means for providing address signals in accordance with the density signal, the capacitance signal and the temperature signal, and memory means having stored within it different values of fractional volumes of at least one constituent of the production stream for selecting a stored value in accordance with the address signals and for providing signals corresponding to the selected value as the output signals; and further comprising recording means connected to the memory means for recording the output signals.

5. An analyzer as described in claim 4 in which the radiation responsive means includes a geiger counter responsive to the radiation that had passed through the production stream provides pulses in accordance with the detected gamma radiation, and a count rate meter connected to the geiger counter provides a signal corresponding to the count rate of the pulses from the geiger counter as the density signal.

6. An analyzer as described in claim 5 in which the means for irradiating the production stream with gamma radiation includes a ten microcurie $Cs^{137}$ gamma ray source.

7. A method of analyzing a flowing crude oil production stream in a conduit which comprises the steps of sensing the temperature of the production stream, measuring the capacitance of the production stream, providing a capacitance signal in accordance with the measuring capacitance, measuring the density of the production stream, and determining the quantity of at least one constituent of the production stream in accordance with the sensed temperature, the capacitance signal and the measured density.

8. A method as described in claim 7 in which the density measuring step includes irradiating the production stream with gamma radiation in a manner so that the gamma radiation passes through the production stream, and providing a density signal corresponding to the density of the production stream in accordance with the gamma radiation that has passed through the production stream.

9. A method as described in claim 8 in which the quantity determining step includes providing address signals in accordance with the density signal, the capacitance signal and the sensed temperature, storing different values of fractional volumes of at least one constituent of the production stream, selecting a stored value in accordance with the address signals, and providing signals corresponding to the selected value as output signals corresponding to the quantity of at least one constituent of the production stream, and further comprising the step of recording the output signals.

10. A method as described in claim 9 in which the radiation responsive step includes receiving the radiation that has passed through the production stream with a geiger counter, providing pulses in accordance with the received gamma radiation, and providing a signal corresponding to the count rate of the pulses from the geiger counter as the density signal.

* * * * *